US012159403B2

(12) United States Patent
Madabhushi et al.

(10) Patent No.: US 12,159,403 B2
(45) Date of Patent: Dec. 3, 2024

(54) COMBINATION OF FEATURES FROM BIOPSIES AND SCANS TO PREDICT PROGNOSIS IN SCLC

(71) Applicants: Case Western Reserve University, Cleveland, OH (US); University Hospitals Cleveland Medical Center, Cleveland, OH (US); The United States Government as Represented by The Department of Veteran Affairs, Washington, DC (US)

(72) Inventors: Anant Madabhushi, Shaker Heights, OH (US); Cristian Barrera, Shaker Heights, OH (US); Mohammadhadi Khorrami, Cleveland Heights, OH (US); Prantesh Jain, Cleveland, OH (US); Afshin Dowlati, Solon, OH (US)

(73) Assignee: The United States Government as Represented by The Department of Veteran Affairs, Washington, DC (US)

( * ) Notice: Subject to any disclaimer, the term of this patent is extended or adjusted under 35 U.S.C. 154(b) by 289 days.

(21) Appl. No.: 17/670,817

(22) Filed: Feb. 14, 2022

(65) Prior Publication Data

US 2022/0405917 A1 Dec. 22, 2022

Related U.S. Application Data

(60) Provisional application No. 63/212,263, filed on Jun. 18, 2021.

(51) Int. Cl.
*G16H 10/40* (2018.01)
*A61B 5/00* (2006.01)
(Continued)

(52) U.S. Cl.
CPC .......... *G06T 7/0012* (2013.01); *A61B 5/7264* (2013.01); *A61B 5/7275* (2013.01);
(Continued)

(58) Field of Classification Search
CPC ..... A61B 2576/02; A61B 5/08; A61B 5/7264; A61B 5/7267; A61B 5/7275; A61B 6/032;
(Continued)

(56) References Cited

U.S. PATENT DOCUMENTS

2004/0087772 A1* 5/2004 Pastan .................. A61K 39/461
530/388.22
2012/0082362 A1* 4/2012 Diem ..................... A61B 5/418
382/133
(Continued)

OTHER PUBLICATIONS

Charlems Alvarez-Jimenez, "Identifying Cross-Scale Associations between Radiomic and Pathomic Signatures of Non-Small Cell Lung Cancer Subtypes: Preliminary Results," Dec. 7, 2020, Cancers 2020, 12, 3663; doi:10.3390, pp. 1-13.*
(Continued)

*Primary Examiner* — Omar S Ismail
(74) *Attorney, Agent, or Firm* — Eschweiler & Potashnik, LLC

(57) ABSTRACT

The present disclosure relates to a non-transitory computer-readable medium storing computer-executable instructions that, when executed, cause a processor to perform operations, including generating an imaging data set having both scan data and digitized biopsy data from a patient with small cell lung cancer (SCLC). Scan derived features are extracted from the scan data and biopsy derived features are extracted from the digitized biopsy data. A radiomic-pathomic risk score (RPRS) is calculated from one or more of the scan derived features and one or more of the biopsy derived
(Continued)

features. The RPRS is indicative of a prognosis of the patient.

20 Claims, 8 Drawing Sheets

(51) Int. Cl.
*G06T 7/00* (2017.01)
*G06T 7/40* (2017.01)
*G16H 30/40* (2018.01)
*G16H 50/20* (2018.01)
*G16H 50/30* (2018.01)

(52) U.S. Cl.
CPC ............... *G06T 7/40* (2013.01); *G16H 10/40* (2018.01); *G16H 30/40* (2018.01); *G16H 50/20* (2018.01); *G16H 50/30* (2018.01); *G06T 2207/10081* (2013.01); *G06T 2207/20081* (2013.01); *G06T 2207/30024* (2013.01); *G06T 2207/30061* (2013.01); *G06T 2207/30096* (2013.01)

(58) Field of Classification Search
CPC .................. A61B 6/037; A61B 6/5217; G06T 2207/10056; G06T 2207/10081; G06T 2207/10088; G06T 2207/10104; G06T 2207/10108; G06T 2207/10116; G06T 2207/20076; G06T 2207/20081; G06T 2207/20084; G06T 2207/30024; G06T 2207/30061; G06T 2207/30064; G06T 2207/30096; G06T 7/0012; G06T 7/11; G06T 7/40; G06T 7/41; G06T 7/42; G06T 7/45; G16H 10/40; G16H 30/40; G16H 50/20; G16H 50/30
See application file for complete search history.

(56) References Cited

U.S. PATENT DOCUMENTS

| | | | | |
|---|---|---|---|---|
| 2012/0143805 | A1* | 6/2012 | Gold | G01N 33/57423 706/20 |
| 2012/0328178 | A1* | 12/2012 | Remiszewski | G06T 11/60 382/133 |
| 2012/0328714 | A1* | 12/2012 | Yang | C12Q 1/6886 424/649 |
| 2013/0137748 | A1* | 5/2013 | Hamamoto | A61P 35/00 435/7.8 |
| 2016/0109539 | A1* | 4/2016 | Mardor | A61B 5/055 600/420 |
| 2016/0110584 | A1* | 4/2016 | Remiszewski | G06V 20/69 382/133 |
| 2017/0071496 | A1* | 3/2017 | Gillies | A61B 5/7264 |
| 2017/0351939 | A1* | 12/2017 | Madabhushi | G06T 7/11 |
| 2018/0336395 | A1* | 11/2018 | Madabhushi | G06V 10/764 |
| 2019/0117801 | A1* | 4/2019 | Donnelly | A61P 35/02 |
| 2020/0388033 | A1* | 12/2020 | Matlock | G06V 20/698 |
| 2020/0410672 | A1* | 12/2020 | Katscher | G06T 7/0012 |
| 2021/0003555 | A1* | 1/2021 | Ferte | G06T 7/0012 |
| 2021/0108270 | A1* | 4/2021 | Mucci | G16B 20/20 |
| 2021/0256699 | A1* | 8/2021 | Wainrib | G06T 7/0012 |
| 2021/0407674 | A1* | 12/2021 | Winkel | G06N 3/08 |
| 2022/0180518 | A1* | 6/2022 | Agus | G06V 10/764 |
| 2022/0405917 | A1* | 12/2022 | Madabhushi | A61B 5/7275 |
| 2023/0027734 | A1* | 1/2023 | Washko, Jr. | G16H 30/40 |
| 2023/0237649 | A1* | 7/2023 | Dillman | G16H 50/30 382/128 |

OTHER PUBLICATIONS

Yucheng Zhang, "Radiomics-based Prognosis Analysis for Non-Small Cell Lung Cancer," Apr. 18, 2017, Scientific Reports|7: 46349, pp. 1-6.*
Eleni Gkika, "Immunohistochemistry and Radiomic Features for Survival Prediction in Small Cell Lung Cancer," Aug. 12, 2020, Frontiers in Oncology, Aug. 2020, vol. 10, Article 1161, pp. 1-9.*
Prantesh Jain et al., "Novel Non-Invasive Radiomic Signature on CT Scans Predicts Response to Platinum-Based Chemotherapy and Is Prognostic of Overall Survival in Small Cell Lung Cancer," Oct. 20, 2021, Frontiers in Oncology, October , vol. 11, Article 744724, pp. 1-10.*
Ruchika Verma et al., "Tumor Habitat-derived Radiomic Features at Pretreatment MRI That are Prognostic for Progression-free Survival in Glioblastoma are Associated with Key Morphologic Attributes at Histopathologic Examination: A Feasibility Study," Radiology: Artificial Intelligence 2020; 2(6):e190168, pp. 1-10.*

* cited by examiner

COMBINATION OF FEATURES FROM BIOPSIES AND SCANS TO PREDICT PROGNOSIS IN SCLC

REFERENCE TO RELATED APPLICATION

This Application claims the benefit of U.S. Provisional application No. 63/212,263, filed on Jun. 18, 2021, the contents of which are hereby incorporated by reference in their entirety.

FEDERAL FUNDING NOTICE

This invention was made with government support under TR000254, CA199374, CA202752, CA208236, CA216579, CA220581, CA239055CA248226, CA254566, HL151277, EB028736, and RR012463 awarded by the National Institutes of Health; W81XWH-20-1-0851, W81XWH-18-1-0440, W81XWH-18-1-0404.W81XWH-19-1-0668, and W81XWH-15-1-0558 awarded by the Department of Defense. The government has certain rights in the invention.

BACKGROUND

Small cell lung cancer (SCLC) is a disease in which cancer cells form in tissues of a lung. SCLC accounts for about 13% to about 15% percent of lung cancers. SCLC is more aggressive than other types of lung cancer, such that SCLC cancer cells grow quickly and travel other parts of the body more easily than other types of lung cancer. As a result, SCLC is usually diagnosed after the cancer has spread throughout the body, making recovery less likely.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

DETAILED DESCRIPTION

Figure 1:
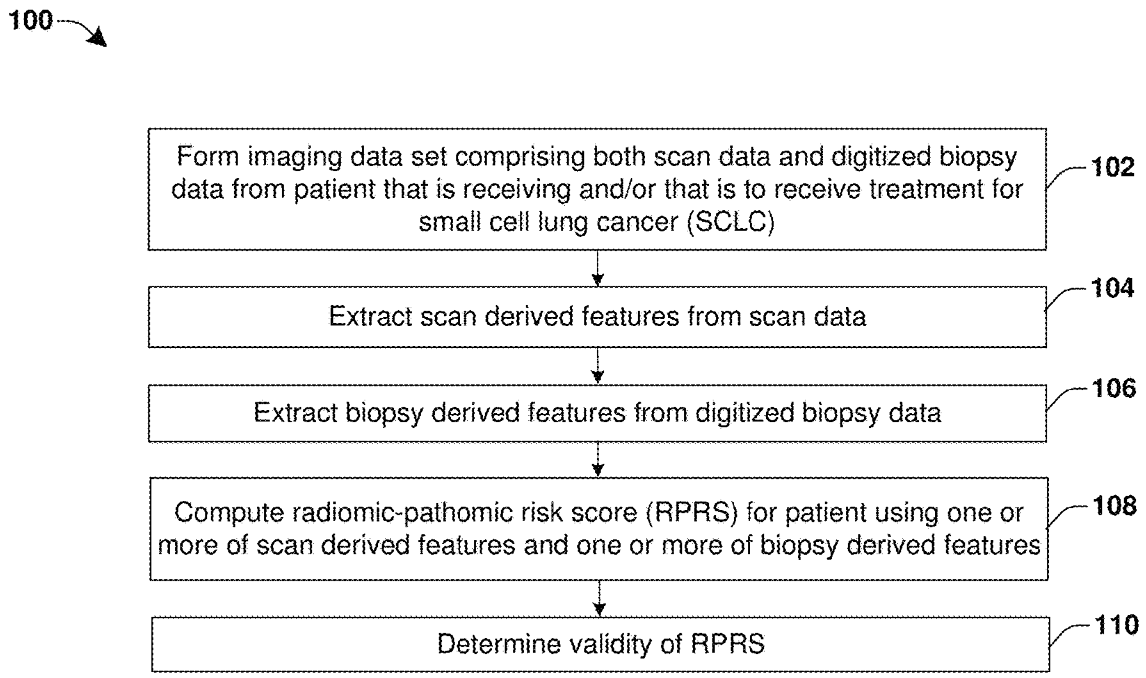
FIG. 1 illustrates some embodiments of a method of predicting a prognosis for a patient having small cell lung cancer (SCLC) utilizing features extracted from both scan data and digitized biopsy data.

The description herein is made with reference to the drawings, wherein like reference numerals are generally utilized to refer to like elements throughout, and wherein the various structures are not necessarily drawn to scale. In the following description, for purposes of explanation, numerous specific details are set forth in order to facilitate understanding. It may be evident, however, to one of ordinary skill in the art, that one or more aspects described herein may be practiced with a lesser degree of these specific details. In other instances, known structures and devices are shown in block diagram form to facilitate understanding.

Small cell lung cancer (SCLC) is an aggressive form of cancer that most commonly arises within the lungs of a patient. SCLC generally responds well to chemotherapy (e.g., to platinum-based chemotherapy). Therefore, chemotherapy is often used as a second option, after surgery, to treat patients having SCLC. However, while chemotherapy may initially be an effective treatment for SCLC, over time resistance to chemotherapy (i.e., chemoresistance) frequently develops in patients with SCLC (e.g., often within a year or so of initial treatment). Chemoresistance leads to a poor prognosis (e.g., an overall 5-year survival of less than 10%) for SCLC, which has not changed significantly in recent years.

It is unclear why some patients with SCLC have and/or develop a resistance to chemotherapy. Additionally, there is a lack of accurate and consistent predictive biomarkers that can be used to guide the treatment of patients with SCLC. This makes it difficult to identify patients that will respond well to chemotherapy, to tell how effective chemotherapy will be at treating a patient with SCLC, and/or to know when alternative treatment options to chemotherapy are appropriate.

The present disclosure relates to a method and apparatus that utilize a combination of radiomic features extracted from radiological scans (e.g., CT scans) and pathomic features extracted from digitized biopsy images (e.g., digitized H&E biopsy images) to predict a prognosis for a patient having SCLC. The method extracts one or more features (e.g., shape and/or texture features) from both scan data and digitized biopsy data. From the extracted features, the method identifies predictive scan features and predictive biopsy features, which are determined to have a disproportionally large impact on a prognosis. A radiomic-pathomic risk score (RPRS), which is indicative of the prognosis, is generated from the predictive scan features and the predictive biopsy features. By forming an RPRS from both the predictive scan features and the predictive biopsy features, an accurate prognosis for a patient can determined thereby guiding treatment options of a health care provider to achieve better results (e.g., to expedite alternative treatment options).

FIG. 1 illustrates some embodiments of a method 100 of predicting a prognosis for a patient having small cell lung cancer (SCLC) utilizing features extracted from both scan data and digitized biopsy data.

At 102, an imaging data set is formed to comprise imaging data from a patient that is receiving and/or that is to receive treatment (e.g., platinum-based chemotherapy) for SCLC cancer. The imaging data set is generated from both scan data (e.g., data from radiological scans) and digitized biopsy data (e.g., digitized H&E slides) of the patient. In some embodiments, the imaging data set may comprise imaging data that includes one or more tumors within a lung of the patient.

At 104, scan derived features are extracted from the scan data. In some embodiments, the scan derived features may comprise shape features and/or texture features extracted from the scan data. The shape features describe a shape of a region of interest (e.g., a tumor) within the scan data, while the texture features describe a texture of the region of interest.

At 106, biopsy derived features are extracted from the digitized biopsy data. In some embodiments, the biopsy derived features may comprise shape features and/or texture features extracted from the digitized biopsy data. The shape features describe a shape of a region of interest within the digitized biopsy data, while the texture features describe a texture of the region of interest.

At 108, a radiomic-pathomic risk score (RPRS) is computed for the patient using one or more of the scan derived features and one or more of the biopsy derived features. The RPRS is indicative of a prognosis of the patient for SCLC (e.g., a response to platinum-based chemotherapy, an overall survival, and/or the like). For example, a high RPRS may indicate that a patient will respond well to treatment, while a low RPRS may indicate that a patient will respond poorly to treatment.

At 110, the RPRS may be evaluated to determine a validity of the RPRS. If the validity of the RPRS is found to be poor, determination of the RPRS can be re-evaluated (e.g., at 108). For example, in some embodiments if the validity of the RPRS is found to be poor, a new RPRS can be determined based on different ones of the scan derived features and/or the biopsy derived features. In various embodiments, the validity of the RPRS may be evaluated by way of clinical data and/or a survival regression model (e.g., a Kaplan Meier survival regression model).

By utilizing the method 100 to determine an RPRS from one or more of both the scan derived features and the biopsy derived features, an accurate prognosis for SCLC (e.g., an overall survival rate, a rate of progression free survival, a response to chemotherapy, or the like) can be made. The accurate prognosis can give health care providers good guidance on treatment options for a patient.

Figure 2:
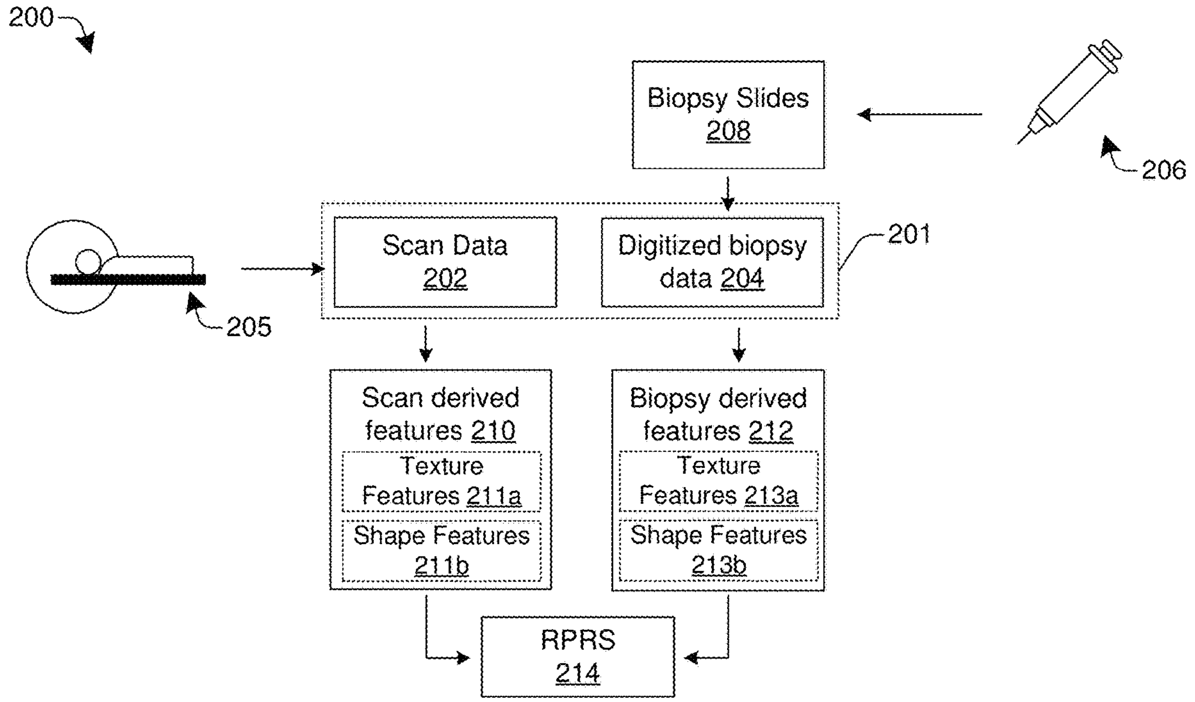
FIG. 2 illustrates a block diagram showing some embodiments of a method of predicting a prognosis for a patient having SCLC utilizing features extracted from both scan data and digitized biopsy data.

FIG. 2 illustrates a block diagram 200 showing some embodiments of a method of predicting a prognosis for a patient having SCLC utilizing features extracted from both scan data and digitized biopsy data.

As shown in block diagram 200, an imaging data set 201 is formed. The imaging data set 201 comprises imaging data for one or more patients that are receiving and/or that are to receive treatment for SCLC. In some embodiments, the imaging data may comprise imaging data corresponding to a tumor that is within a lung of a patient. In some embodiments, the imaging data may comprise baseline imaging data (e.g., imaging data used to make an initial diagnosis of a patient prior to the patient beginning a treatment for SCLC).

The imaging data set 201 comprises both scan data 202 and digitized biopsy data 204. The scan data 202 comprises data obtained from an imaging tool 205 that is configured to take radiological images of a patient. In various embodiments, the scan data 202 may comprise data from x-rays, computerized tomography (CT) scans, magnetic resonance imaging (MRI) scans, positron emission tomography (PET) scans, or the like. The digitized biopsy data 204 comprises data obtained from one or more pathological tissue samples taken from a patient's body. In some embodiments, a biopsy 206 is performed on the patient to obtain a tissue block. The tissue block is sliced into thin slices that are placed on a transparent slide (e.g., a glass slide) to generate biopsy slides 208. The biopsy slides 208 are subsequently converted to a plurality of whole slide images comprising the digitized biopsy data 204. In some embodiments, the digitized biopsy data 204 may comprise digitized images of stained biopsy slides. For example, the digitized biopsy data 204 may comprise digitized H&E (Hematoxylin and Eosin) stain images. In some embodiments, the scan data 202 and the digitized biopsy data 204 may comprise a same tumor (e.g., a single tumor or biopsy). In some such embodiments, the scan data 202 may be obtained prior to a biopsy being performed on the tumor so that the scan data 202 may contain a same region of the tumor as the digitized biopsy data 204.

Scan derived features 210 are extracted from the scan data 202 and biopsy derived features 212 are extracted the digitized biopsy data 204. In various embodiments, the scan derived features 210 may comprise texture features 211*a* (e.g., radiomic texture features) and/or shape based features 211*b* (e.g., radiomic shape based features) extracted from one or more regions of interest within the scan data 202. In various embodiments, the biopsy derived features 212 may comprise texture features 213*a* and/or shape based features 213*b* extracted from one or more regions of interest within the digitized biopsy data 204. In some embodiments, the one or more regions of interest may comprise the tumor.

In some embodiments, the scan derived features 210 may comprise texture features 211*a* and shape based features 211*b* extracted from a first region of interest within the scan data 202 and the biopsy derived features 212 may comprise texture features 213*a* and shape based features 213*b* extracted from a second region of interest within the digitized biopsy data 204. In some embodiments, the first region of interest may overlap the second region of interest, so that the first region of interest and the second region of interest comprise one or more same structural features of a patient. In some embodiments, the scan derived features 210 and/or the biopsy derived features 212 are taken from different pixels through a region of interest (e.g., a sample cell, a tumor, or the like). For example, if a region of interest comprises an area that is approximately 30 pixels by 30 pixels, the scan derived features 210 and/or the biopsy derived features 212 may be extracted from a majority of the pixels (e.g., all of the pixels) in the region of interest, but not from pixel surrounding the region of interest.

The texture features, 211*a* and 213*a*, describe variations over a region of interest (e.g., a surface of a tumor). In some embodiments, the texture features, 211*a* and 213*a*, may be extracted by measuring variations in image intensities between neighboring pixels or voxels (e.g., by measuring a difference in gray scale values of neighboring pixels or voxels) within a region of interest of an image. In such embodiments, a rough textured tumor would have a high rate of variations while a smooth textured tumor would have a low rate of variations.

In some embodiments, the texture features, 211*a* and 213*a*, may be extracted by measuring pixel values (e.g., Hounsfield units for 211*a* and spatial variation of brightness intensity of pixels for 213*a*) within a region of interest and subsequently subjecting the measured pixel values to statistical analysis (e.g., a mean, medium, standard deviation, or the like) to arrive at a texture feature. For example, in some embodiments, the texture features, 211*a* and 213*a*, may be extracted from the scan data 202 and/or the digitized biopsy data 204 using a gray level co-occurrence matrix (GLCM). In such embodiments, the GLCM may determine a distribution of co-occurring pixel values (e.g., Hounsfield units for 211*a* and spatial variation of brightness intensity of pixels for 213*a*) at a given offset, so as to determine how closely associated image signals within a local region are and thus give a measure of texture features within a region of interest. The GLCM is subsequently subjected to statistical analysis (e.g., a mean, medium, standard deviation, or the like) to arrive at a texture feature. In such embodiments, the texture features, 211*a* and 213*a*, may comprise a median value of GLCM entropy, a mean value of GLCM entropy, or the like. In other embodiments, the texture features, 211*a* and 213*a*, may be extracted from the scan data 202 and/or the digitized biopsy data 204 using a gray level difference matrix, a gray level run length matrix, or other similar methods.

The shape based features, 211*b* and 213*b*, describe a size and/or shape of the region of interest (e.g., a three or two dimensional size and/or shape of a tumor). In some embodiments, the shape based features, 211*b* and 213*b*, may be described by Zernike polynomials. In other embodiments, the shape based features, 211*b* and 213*b*, may comprise one or more of compactness (e.g., how much a shape of a tumor resembles that of a sphere), spherical disproportion (e.g., a ratio of a surface area of a tumor region to a surface area of a sphere with a same volume as the tumor region), sphericity (e.g., a ratio of a perimeter of the tumor region to a perimeter of a circle with a same surface area as the tumor region), surface area, or the like.

A radiomic-pathomic risk score (RPRS) 214 is determined from one or more of the scan derived features 210 and one or more of the biopsy derived features 212. In some embodiments, the RPRS 214 may be determined using a machine learning classifier comprising a risk score calculation model. In some embodiments, the risk score calculation model may be formed using a machine learning algorithm that acts upon the scan derived features 210 and the biopsy derived features 212. For example, in some embodiments a survival regression model may be trained by utilizing both the scan derived features 210 and the biopsy derived features 212 to determine a risk score calculation model that is configured to calculate the RPRS based upon a survival time of the patient. In such embodiments, a value of the RPRS 214 may correspond to the survival time (e.g., a high survival time may indicate a low RPRS and a low survival time may indicate a high RPRS).

Figure 3:
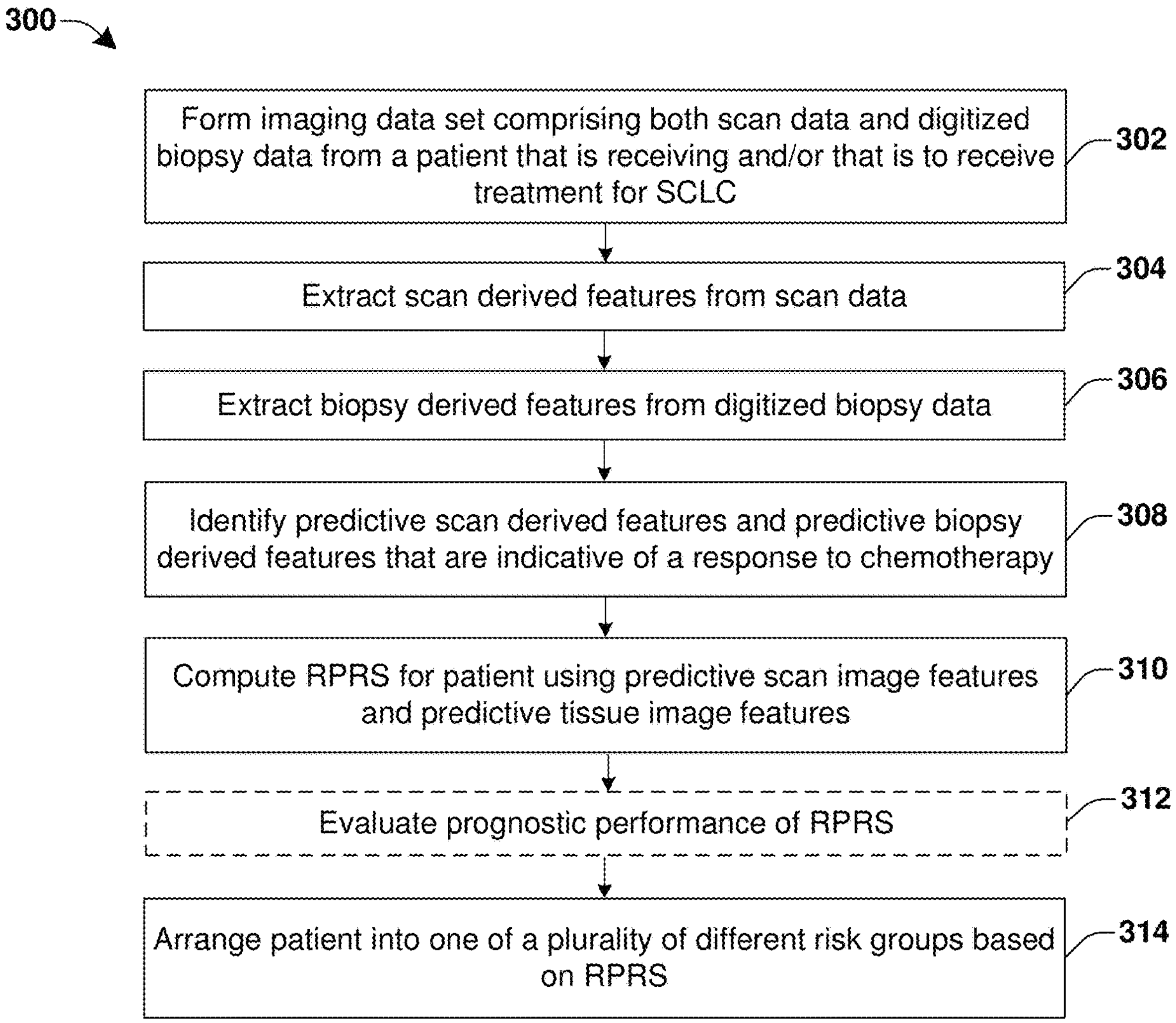
FIG. 3 illustrates some additional embodiments of a method of predicting a prognosis for a patient having SCLC utilizing features extracted from both scan data and digitized biopsy data.

FIG. 3 illustrates some additional embodiments of a method 300 of predicting a prognosis for a patient having SCLC utilizing features extracted from both scan data and digitized biopsy data.

At 302, an imaging data set is formed to comprise imaging data for a patient that is receiving and/or that is to receive chemotherapy (e.g., platinum-based chemotherapy) for SCLC. The imaging data set comprises scan data from radiological scans and digitized biopsy data from digitized biopsy slides. In some embodiments, the imaging data set may comprise imaging data of one or more tumors within the patient's lung. In some embodiments, the imaging data set comprises and/or is pre-treatment imaging data.

At 304, scan derived features are extracted from the scan data. In some embodiments, the scan derived features may comprise shape features and/or texture features extracted from the scan data.

At 306, biopsy derived features are extracted from the digitized biopsy data. In some embodiments, the biopsy derived features may comprise shape features and/or texture features extracted from the digitized biopsy data.

At 308, predictive scan derived features and predictive biopsy derived features are identified from the scan derived features and the biopsy derived features. The predictive scan derived features and the predictive biopsy derived features are a subset of the scan derived features and the biopsy derived features that are determined to be indicative of a prognosis of the patient to SCLC.

At 310, a radiomic-pathomic risk score (RPRS) is determined from the predictive scan derived features and the predictive biopsy derived features. The RPRS describes a relation between a prognosis of the patient and both the predictive scan derived features and the predictive biopsy derived features (e.g., so that different radiomic-pathomic risk scores are indicative of different outcomes for the patient).

At 312, a prognostic performance of the RPRS may be evaluated. In various embodiments, the prognostic performance may be evaluated according to criteria such as a change in size of a tumor, survival rates of patients having the tumor, or the like. In some embodiments, the prognostic performance of the RPRS may be evaluated as part of a single process that initially determines the RPRS (e.g., as part of a training process of a survival regression model).

At 314, the patient is arranged into one of a plurality of different risk groups based on the RPRS. The plurality of different risk groups respectively correlate to different prognostic outcomes. For example, if the RPRS is low the patient may be placed into a first risk group denoting a positive prognosis to treatment (e.g., a high overall survival rate, a high rate of progression free survival, a good response to chemotherapy, or the like), while if the RPRS is high the patient may be placed into a second risk group denoting a negative prognosis to treatment (e.g., a low overall survival rate, a low rate of progression free survival, a poor response to chemotherapy, or the like).

Figure 4:
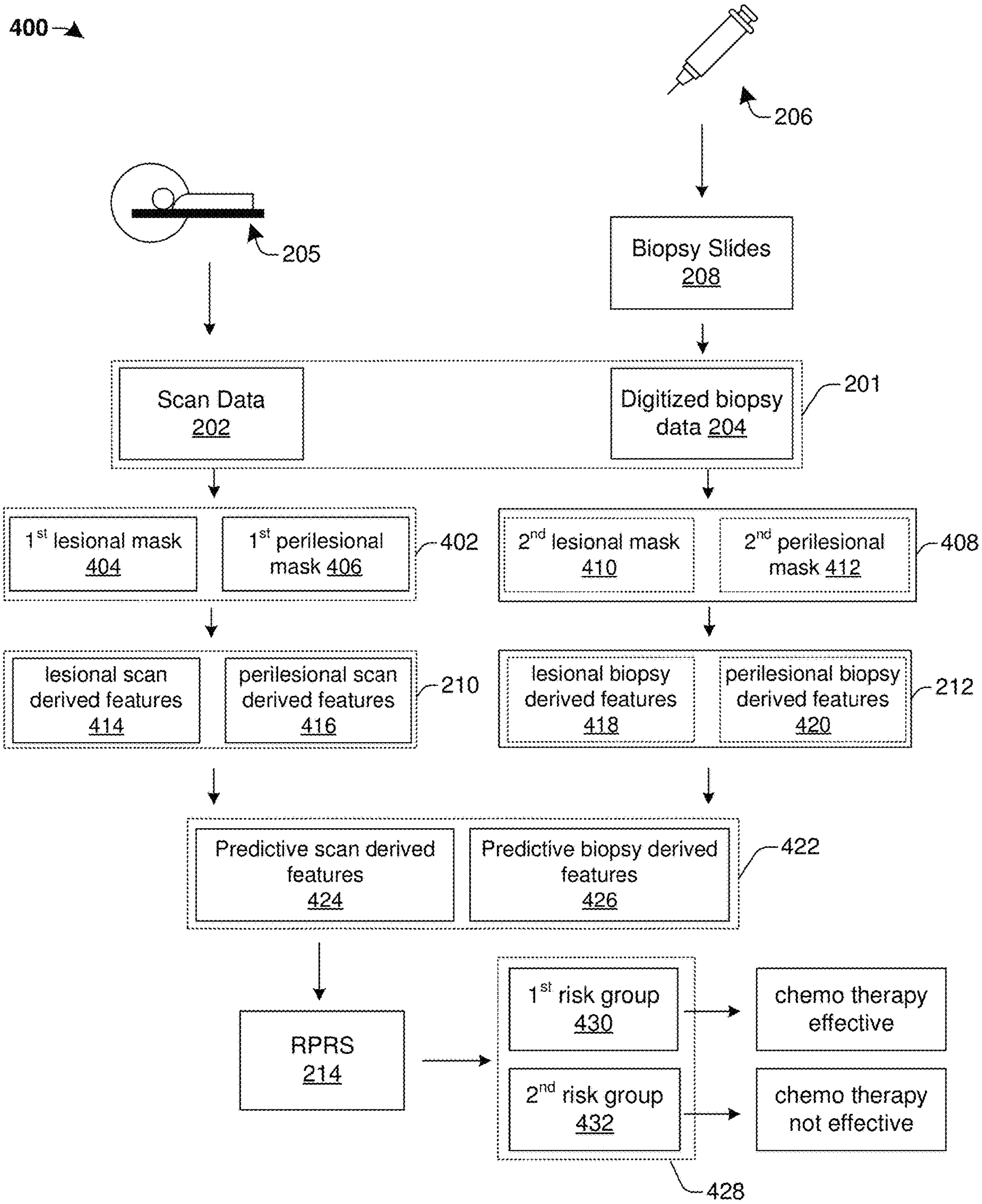
FIG. 4 illustrates a block diagram showing some embodiments of a method of predicting a prognosis for a patient having SCLC utilizing features extracted from both scan data and digitized biopsy data.

FIG. 4 illustrates a block diagram 400 showing some embodiments of a method of predicting a prognosis for a patient having SCLC utilizing features extracted from both scan data and digitized biopsy data.

As shown in block diagram 400, an imaging data set 201 is formed. The imaging data set 201 comprises imaging data for a patient that is receiving and/or that is to receive treatment (e.g., chemoradiation) for SCLC. In some embodiments, the imaging data set 201 may comprise both scan data 202 from a radiological image and digitized biopsy data 204 from a biopsy.

In some embodiments, the scan data 202 is used to generate first masks 402 respectively having data from different regions of the scan data 202. In some embodiments, the first masks 402 may comprise a first lesional mask 404 and a first perilesional mask 406 associated with an image of the patient. In some embodiments, the first lesional mask 404 may be formed by removing imaging data relating to parts of an image that are around a tumoral region comprising a tumor, so that the first lesional mask 404 predominately has intra-lesional data within a tumor. Similarly, the first perilesional mask 406 may be formed by removing data relating to parts of an image that are within a tumoral region, so that the first perilesional mask 406 predominately has data relating to a peritumoral region around the tumoral region (e.g., around the tumor). In some embodiments, the first perilesional mask 406 may comprise lung tissue that surrounds the tumor. In some embodiments, the first perilesional mask 406 may have a width of approximately 5 mm surrounding an associated tumor. In others embodiments, the first perilesional mask 406 may have a width of approximately 10 mm, approximately 15 mm, or other similar values, surrounding an associated tumor.

In some embodiments, the digitized biopsy data 204 is used to generate second masks 408 having data from different regions of the digitized biopsy data 204. In some embodiments, the second masks 408 may comprise a second lesional mask 410 and a second perilesional mask 412 associated with an image of the patient. In some embodiments, the second lesional mask 410 may be formed by removing imaging data relating to parts of an image that are around a tumoral region (e.g., around a tumor), so that the second lesional mask 410 predominately has intra-lesional data within a tumor. Similarly, the second perilesional mask 412 may be formed by removing data relating to parts of an image that are within a tumoral region, so that the second perilesional mask 412 predominately has data relating to a region around the tumor. In other embodiments, second masks may not be formed from the digitized biopsy data 204 since the digitized biopsy data 204 may not contain significant data within a peritumoral region.

Scan derived features 210 are extracted from the first masks 402. In some embodiments, the scan derived features 210 may comprise lesional scan derived features 414 and perilesional scan derived features 416. The lesional scan derived features 414 may be extracted from the first lesional mask 404 and the perilesional scan derived features 416 may be extracted from the first perilesional mask 406. In some embodiments, the scan derived features 210 may be extracted from the first masks 402 using a gray level co-occurrence matrix (GLCM). In such embodiments, the lesional scan derived features 414 may comprise a skew (statistical representation) of GLCM entropy within the first lesional mask 404, a kurtosis (statistical representation) of GLCM entropy within the first lesional mask 404, or the like, while the perilesional scan derived features 416 may comprise a skew (statistical representation) of GLCM entropy within the first perilesional mask 406, a kurtosis (statistical representation) of GLCM entropy within the first perilesional mask 406, or the like.

In some embodiments, biopsy derived features 212 are extracted from the second masks 408. In some embodiments, the biopsy derived features 212 may comprise lesional biopsy derived features 418 (e.g., shape-based features) extracted from the second lesional mask 410 and perilesional biopsy derived features 420 (e.g., shape-based features) extracted from the second perilesional mask 412.

Predictive features 422 are determined from the scan derived features 210 and the biopsy derived features 212. In some embodiments, the predictive features 422 may comprise predictive scan derived features 424 determined from the scan derived features 210 and predictive biopsy derived features 426 determined from the biopsy derived features 212. The predictive features 422 are a subset of the scan derived features 210 and the biopsy derived features 212, which are most predictive of a patient's prognosis (e.g., features that have a high correlation to a response of SCLC to chemotherapy, a high correlation to overall survival, or the like). In some embodiments, the scan derived features 210 may comprise a first number of features, while the predictive scan derived features 424 may comprise a second number of features that is different than (e.g., smaller than) the first number of features.

In some embodiments, the predictive features 422 may be identified using a machine learning classifier (e.g., a machine learning algorithm) that operates upon a set (e.g., having over 100 features) comprising the scan derived features 210 and the biopsy derived features 212. For example, in some embodiments the predictive features 422 may be identified by operating upon the set using a random forest algorithm. In some such embodiments, the random forest algorithm may form a plurality of decision trees through Boruta algorithm (e.g., hundreds or thousands of decision trees) using a random extraction of observations from a dataset and a random extraction of the scan derived features 210 and the biopsy derived features 212.

In some embodiments, the predictive features 422 are the features that are correlated with endpoints including both overall survival and a response to treatment (e.g., chemotherapy). In such embodiments, the predictive features 422 may be determined using a plurality of machine learning classifier models. For example, the predictive features 422 may be determined using a first machine learning classifier model that correlates to overall survival and a second machine learning classifier model that correlates to a response to treatment (e.g., chemotherapy).

An RPRS 214 may be determined from both the predictive scan derived features 424 and the predictive biopsy derived features 426. In some embodiments the RPRS 214 may be determined using a machine learning algorithm comprising a risk score calculation model configured to operate upon the predictive scan derived features 424 and the predictive biopsy derived features 426. In some embodiments, the risk score calculation model may comprise a prognostic model. In such embodiments, a high RPRS 214 indicates a higher risk of death (e.g., regardless of treatment), as the chosen endpoint to prognosticate is overall survival (OS). In some embodiments, the risk score calculation model may comprise a predictive model. In such embodiments, the predictive model is trained using response to chemo (e.g., a good response or a bad response) and outputs an RPRS 214 that is indicative of a responder and non-responder.

In some embodiments the machine learning algorithm may comprise a survival regression model that utilizes both the predictive scan derived features 424 and the predictive biopsy derived features 426 to determine a risk score calculation model that is configured to calculate the RPRS 214 based upon a survival time of patients. In such embodiments, the RPRS 214 may correspond to the survival time (e.g., a high survival time may indicate a low risk score and a low survival time may indicate a high risk score). In some embodiments, the survival regression model may comprise an elastic net regularized Cox regression (e.g., an elastic net regularized Cox proportional hazards model) that is trained using the predictive scan derived features 424 and the predictive biopsy derived features 426 to derive the RPRS 214. In some embodiments, the elastic net regularized Cox regression fits the predictive scan derived features 424 and the predictive biopsy derived features 426 and gives each one a penalty value (e.g., a weight that gives the value either more influence or less influence). In some embodiments, the penalty value may comprise a positive coefficient that indicates a bad prognosis (e.g., assuming that high level is high risk) and a negative coefficient is a good prognosis. The coefficients then are multiplied with the features and a single column is produced. The single column is a single value per patient, which is the RPRS 214.

In some embodiments, the patient is arranged into one of a plurality of different risk groups 428 based on the RPRS 214. For example, if the RPRS 214 is below a risk score threshold the patient may be grouped into a first risk group 430, while if the RPRS 214 is above the risk score threshold the patient may be grouped into a second risk group 432. The first risk group 430 is indicative of a positive prognosis (e.g., a 1-year survival rate of over 50%). The second risk group 432 is indicative of a negative prognosis (e.g., a 1-year survival rate of less than 50%).

Figure 5:
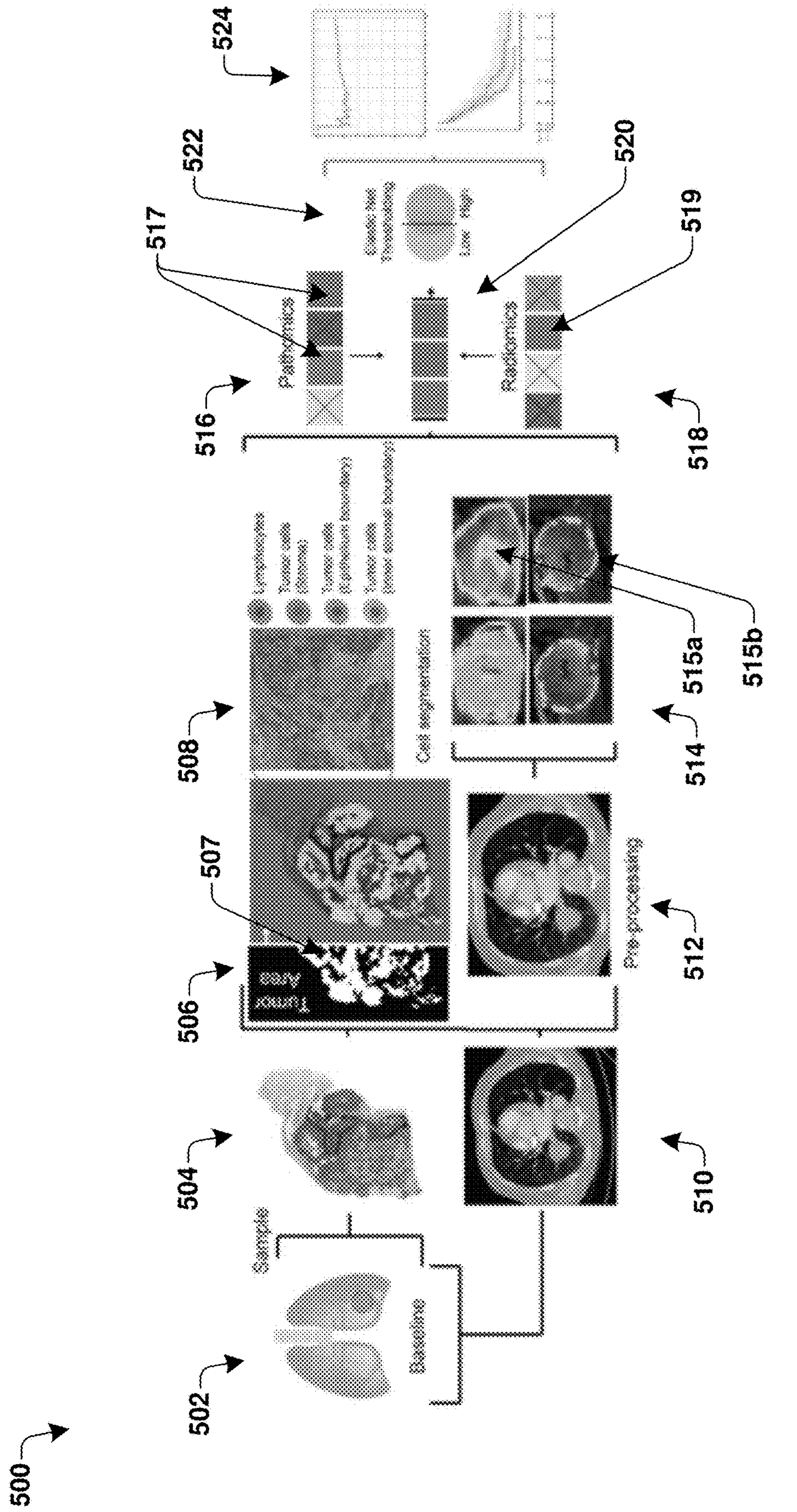
FIG. 5 illustrates a diagram showing some embodiments of a method of predicting a prognosis for a patient having SCLC utilizing features extracted from both scan data and digitized biopsy data.

FIG. 5 illustrates a diagram 500 showing some embodiments of a method of predicting a prognosis for a patient having SCLC utilizing features extracted from both scan data and digitized biopsy data.

As shown in diagram 500, a patient 502 having SCLC is identified. The patient 502 may be a patient that has not undergone chemotherapy treatment. A radiological image comprising scan data 510 is taken of the patient 502 and a tissue sample 504 is taken from the patient 502.

The tissue sample 504 may be placed on a plurality of slides. Images of the plurality of slides may subsequently be taken to form digitized biopsy data 506 comprising a plurality of whole slide images (WSIs). In some embodiments, a quality control operation is performed on the plurality of whole slide images through a deep learning approach. In some embodiments, the deep learning approach may be based on tissue detection and artifact removal with a statistical assessment. In various embodiments, the deep learning approach may verify that the H&E images are readable, verify that the H&E images do not have significant noise (i.e., are blurry), indicate which images are susceptible to noise and may carry difficulty for posterior annotations, or the like.

A tumor area 507 is identified from within the digitized biopsy data 506. The tumor area 507 may be segmented to form a segmented tumor region 508 that identifies different cells within parts of the tumor area 507. In some embodiments, the segmentation process tiles respective ones of the plurality of whole slide images into a plurality of patches. In some embodiments, the segmentation of the plurality of patches may identify lymphocytes, stroma tumor cells, epithelium tumor cells, inner stromal tumor cells, or other similar regions. In some embodiments, the segmentation process may apply a nuclei segmentation model based on deep learning to the whole slide images to identify cells according to a binary mask (e.g., a mask identifying a nuclei of a cell as a 1 and background tissue as a 0). In some additional embodiments, the nuclei segmentation model may use multiple scales and/or color un-mixing processes to detect nuclei. In some embodiments, the segmentation may remove parts of the whole slide images that are outside of the lung. In some embodiments, a machine learning algorithm may also be applied to each patch to distinguish tumor-infiltrating lymphocytes from tumor cells. In some embodiments, this algorithm generates two binary masks, one highlighting the lymphocytes and the other the non-lymphocyte cells. In other embodiments, the segmentation may be performed by an expert pathologist to highlight the tumor.

A plurality of biopsy derived features 516 (e.g., pathomic features) are extracted from the segmented tumor region 508. In some embodiments, the plurality of biopsy derived features 516 may comprise shape features and texture features. In some embodiments, the shape features may use Zernike polynomials to describe variations found on tumor cells. In some embodiments, the textual features may comprise Haralick features (e.g., an entropy of intratumoral Haralick feature) determined using pixel intensities of the tumor cells, a median of intratumoral Laws texture feature, and an intratumoral low-frequency Gabor feature, or other similar features. In other embodiments, the plurality of biopsy derived features 516 consist of shape features without texture features. It has been appreciated that within the digitized biopsy data 506, shape features may be more predictive of a prognosis of a patient and therefore that limiting the plurality of biopsy derived features 516 to shape features may improve an accuracy of a prognosis. In some embodiments, lymphocytes may be removed from the binary mask to improve an accuracy of the plurality of biopsy derived features 516.

Predictive biopsy derived features 517 are identified from the plurality of biopsy derived features 516. The predictive biopsy derived features 517 comprise a subset of the plurality of biopsy derived features 516 that have a high correlation to a patient's prognosis. In some embodiments, the predictive biopsy derived features 517 are identified using a random forest selection and linear regression model, a Boruta algorithm, or the like.

In some embodiments, pre-processing is performed on the scan data 510 to generate a processed radiological image 512. In various embodiments, pre-processing may comprise verifying that the scan data 510 is readable, verifying that the scan data 510 does not have significant noise (i.e., is blurry), removing parts of the scan data 510 that are outside of a lung, employing expert pathologists to highlight a tumor in the scan data 510, or the like.

In some embodiments, masks 514 may be formed from the processed radiological image 512. The masks 514 may comprise a lesional mask **515*a* and perilesional mask 515*b*. A plurality of scan derived features 518 are extracted from the masks 514 (e.g., from the lesional mask 515*a* and the perilesional mask 515*b*). In some embodiments, the plurality of scan derived features 518 may comprise textual and/or spatial features identified from the masks 514. In some embodiments, the shape features may use Zernike polynomials to describe the variation found on the tumor cells. In some embodiments, the textual features may comprise Haralick features (e.g., an entropy of intratumoral Haralick feature) determined using pixel intensities of the tumor cells, a median of intratumoral Laws texture feature, and an intratumoral low-frequency Gabor feature, or other similar features. In other embodiments, the plurality of scan derived features 518 consist of texture features without shape features. It has been appreciated that within the scan data 510, texture features may be more predictive of a prognosis of a patient and therefore that limiting the plurality of scan derived features 518** to texture features may improve an accuracy of a prognosis.

Predictive scan derived features 519 are identified from the plurality of scan derived features 518. The predictive scan derived features 519 comprise a subset of the plurality of scan derived features 518. In some embodiments, the predictive scan derived features 519 are identified using a random forest selection and linear regression model, a Boruta algorithm, or the like.

A regression model is applied to the predictive biopsy derived features 517 and the predictive scan derived features 519 to determine a radiomic-pathomic risk score (RPRS) 520. In some embodiments, the regression model may generate the RPRS 520 as a linear combination of the predictive biopsy derived features 517 and the predictive scan derived features 519 weighted by coefficients. In some embodiments, the regression model may comprise a first number of predictive biopsy derived features (e.g., 7) and a second number of predictive image derived features (e.g., 8) that is different than the first number of predictive biopsy derived features.

The RPRS 520 correlates to different prognostic outcomes of the patient 502. For example, in some embodiments the RPRS 520 may to correlate to an overall survival of the patient 502. In such embodiments, the RPRS 520 may have a hazard ratio of 2.5 with a 95% confidence interval for HR, a confidence interval of between 1.3 and 4.9, and a P-value of 0). In other embodiments, the RPRS 520 may correlate to a high rate of progression free survival. In yet other embodiments, the RPRS 520 may correlate to a good response to chemotherapy. In yet other embodiments, the RPRS 520 may correlate to a high rate of chemo-sensitivity (e.g., with an area under curve of 0.76 and a PRC of 0.81).

In some embodiments, the RPRS 520 may be compared to a risk score threshold to classify a patient into different risk groups. In some embodiments, the RPRS 520 may be compared using elastic net thresholding 522 to form binary risk groups. The binary risk groups improve an ability of the method to identify patients that are of higher risk of death and would benefit from stronger treatments and low risk groups which need less severe treatments. The different risk groups may be subsequently evaluated 524 to determine a propriety of the different risk groups. In various embodiments, the different risk groups may be evaluated using survival analysis (e.g., a Kaplan Meier survival analysis configured to generate a Kaplan-Meier curve), changes in tumor size, or other similar methods.

Figure 6:
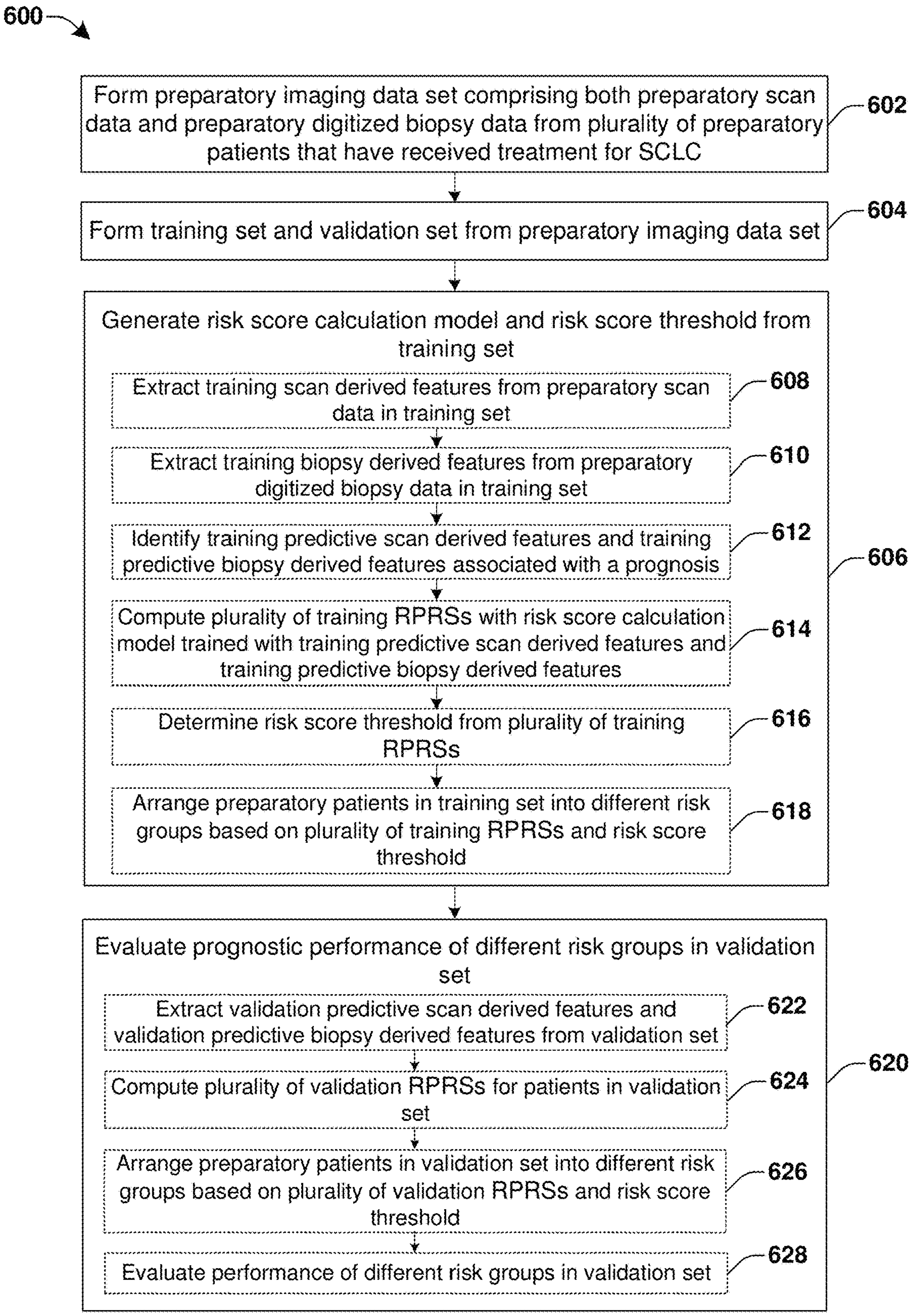
FIG. 6 illustrates some additional embodiments of a method of generating a risk score calculation model configured to generate a radiomic-pathomic risk score (RPRS) corresponding to a prognosis for a patient having SCLC.

FIG. 6 illustrates some additional embodiments of a method 600 of generating a risk score calculation model configured to generate a radiomic-pathomic risk score (RPRS) corresponding to a prognosis for a patient having SCLC.

At 602, a preparatory imaging data set if formed to comprise imaging data for a plurality of preparatory patients that have received treatment (e.g., platinum-based chemotherapy) for SCLC. The preparatory imaging data set may comprise both preparatory scan data from radiological scans and preparatory digitized biopsy data from digitized biopsy slides (e.g., whole slide images).

At 604, a training set and a validation set are formed from the preparatory imaging data set. The training set comprises imaging data from a first group of the plurality of preparatory patients within the preparatory imaging data set and the validation set comprises imaging data from a second group of the plurality of preparatory patients within the preparatory imaging data set.

At 606, a risk score calculation model and a risk score threshold are generated from the training set. In various embodiments, the risk score calculation model and a risk score threshold may be generated according to acts 608-618.

At 608, training scan derived features are extracted from preparatory scan data of the first group of the plurality of preparatory patients within the training set.

At 610, training biopsy derived features are extracted from preparatory digitized biopsy data of the first group of the plurality of preparatory patients within the training set.

At 612, training predictive scan derived features and training predictive biopsy derived features are identified from the training scan derived features and the training biopsy derived features in the training set.

At 614, a plurality of training radiomic-pathomic risk scores (RPRSs) are calculated from the training predictive scan derived features and the training predictive biopsy derived features. The plurality of training RPRSs respectively correspond to a patient of the first group of the plurality of preparatory patients. In some embodiments, the plurality of training RPRSs are determined using a risk score calculation model that is formed by training a machine learning model (e.g., a survival regression model) using the training predictive scan derived features and the training predictive biopsy derived features.

At 616, a risk score threshold is determined from the plurality of training RPRSs. In some embodiments, the risk score threshold may comprise a median risk score of the plurality of training RPRSs.

At 618, the first group of the plurality of preparatory patients in the training set are arranged into different risk groups based upon the plurality of training RPRSs and the risk score threshold. For example, if a training RPRS is below the risk score threshold a corresponding patient may be placed into a first risk group, while if a training RPRS is above the risk score threshold a corresponding patient may be placed into a second risk group. The plurality of different risk groups respectively correlate to different prognostic outcomes of a patient (e.g., to chemotherapy, for overall survival, etc.).

At 620, a prognostic performance of the different risk groups is evaluated by the second group of the plurality of preparatory patients within the validation set. In various embodiments, the prognostic performance of the different risk groups may be evaluated according to acts 622-628.

At 622, validation predictive scan derived features and validation predictive biopsy derived features are extracted from preparatory imaging data of the second group of the plurality of preparatory patients within the validation set.

At 624, a plurality of validation risk scores are calculated using the validation predictive scan derived features and the validation predictive biopsy derived features for each patient of the second group of the plurality of preparatory patients. In some embodiments, the plurality of validation RPRSs are determined using the risk score calculation model developed with the training set.

At 626, the second group of the plurality of preparatory patients in the validation set are arranged into the plurality of different risk groups based on their validation RPRS.

At 628, a prognostic performance of second group of the plurality of preparatory patients within the plurality of different risk groups is evaluated. In some embodiments, the prognostic performance corresponds to a survival rate (e.g., a 1-year survival rate, a 5-year survival rate, or the like) for the second group of the plurality of preparatory patients within the first risk group and within the second risk group. In some embodiments, the prognostic performance may be evaluated using clinical data.

Figure 7:
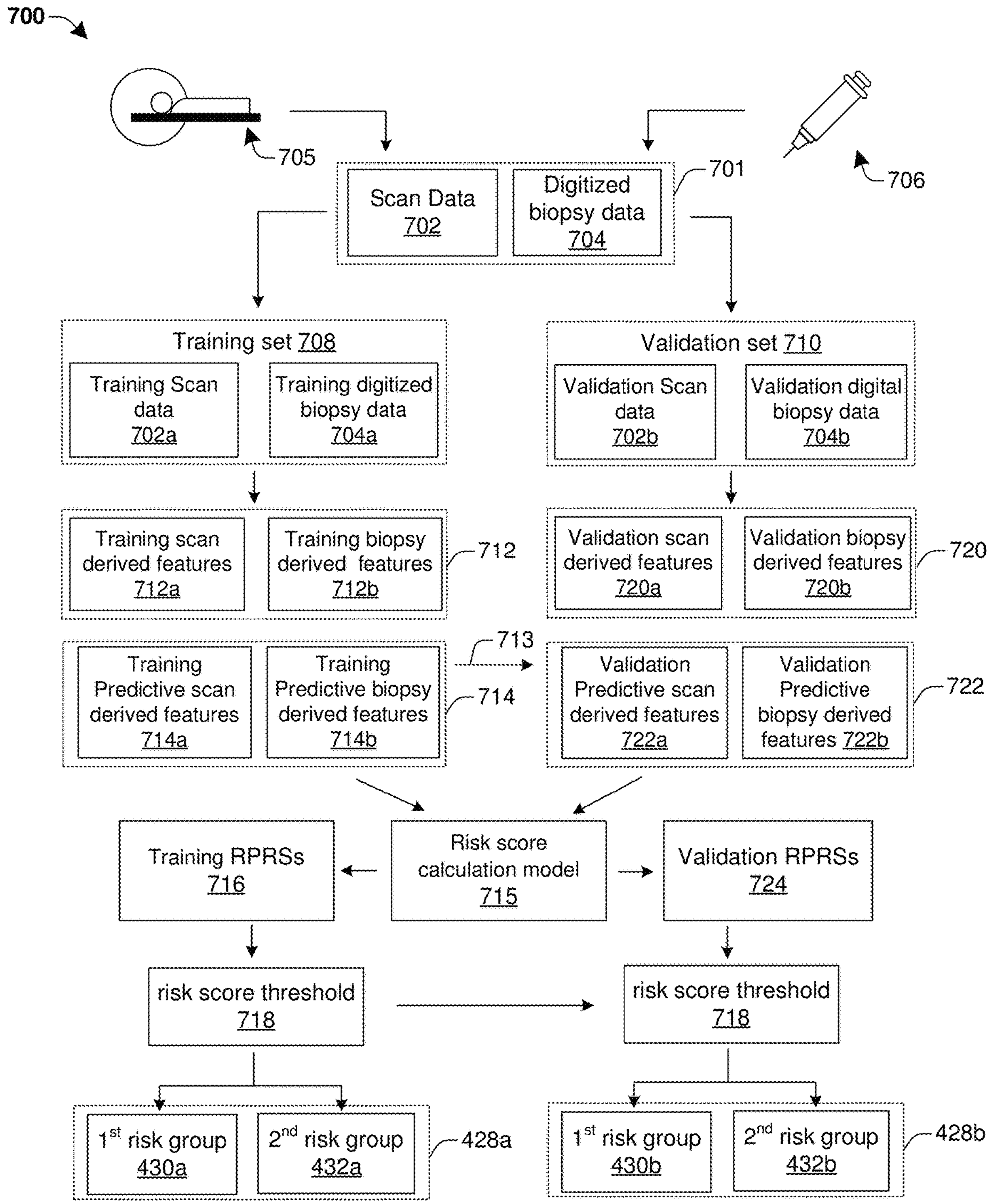
FIG. 7 illustrates a block diagram showing some embodiments of a method of generating a risk score calculation model configured to generate an RPRS corresponding to a prognosis for a patient having SCLC.

FIG. 7 illustrates a block diagram 700 showing some embodiments of generating a risk score calculation model configured to generate a radiomic-pathomic risk score (RPRS) corresponding to a prognosis for a patient having SCLC.

As shown in block diagram 700, a preparatory imaging data set 701 is formed. The preparatory imaging data set 701 comprises imaging data for a plurality of preparatory patients that have subsequently received treatment (e.g., platinum-doublet chemotherapy) for SCLC. In some embodiments, the preparatory imaging data set 701 comprises preparatory scan data 702 and preparatory digitized biopsy data 704. The preparatory scan data 702 comprises data obtained from an imaging tool 705 that is configured to take radiological images of a patient. In some embodiments, the preparatory digitized biopsy data 704 is obtained by performing a biopsy 706 on a patient to obtain a tissue block, slicing the tissue block into thin slices that are placed on transparent slides to generate biopsy slides, and subsequently converting the biopsy slides to a plurality of whole slide images.

In some embodiments, the plurality of preparatory patients may comprise responders (e.g., patients that had an objective response and/or stable disease per RECISTS (Response evaluation criteria in solid tumors) v1.1, for a response during of greater than or equal to approximately 6 months) and non-responders (e.g., patients that had no progression of disease within 6 months). In some embodiments, the plurality of preparatory patients may have early stage or late stage SCLC. In some embodiments, the plurality of preparatory patients may comprise patients that have accessible pathological SCLC evidence, that have a diagnostic thoracic CT scan in an axial view, that have a solitary pulmonary nodule/mass, that have both an H&E sample and a CT scan, that have overall survival information available, and/or that have information relating to a response to treatment available. In some embodiments, the plurality of preparatory patients may also not have a sample biopsy history before imaging, be without an isolated lesion on CT scans, have poor quality CT or H&E scans, and/or have samples with insufficient tumor/tissue region.

The preparatory imaging data set 701 may be divided into a training set 708 comprising data from a first group of the plurality of preparatory patients and a validation set 710 (i.e., a testing set) comprising data from a second group of the plurality of preparatory patients. In some embodiments, the division of the preparatory imaging data set 701 may be performed so that the training set 708 has an equal number of responders and non-responders.

Training derived features 712 are extracted from both training scan data 702*a* and training digitized biopsy data 704*a* in the training set 708. In some embodiments, the training derived features 712 comprise training scan derived features 712*a* extracted from the training scan data 702*a* and training biopsy derived features 712*b* extracted from the training digitized biopsy data 704*a* of each preparatory patient of the second group of the plurality of preparatory patients. For example, first training scan derived features and first training biopsy derived features are extracted from imaging data of a first patient, second training scan derived features and second training biopsy derived features are extracted from imaging data of a second patient, etc. In some embodiments, the training scan derived features 712*a* include texture features extracted from lesional and/or perilesional masks of the training scan data 702*a*. In some embodiments, the training biopsy derived features 712*b* include shape features extracted from the training digitized biopsy data 704*a*.

In some embodiments, for each preparatory patient a first number of training scan derived features 712*a* may be extracted from the training scan data 702*a* and a second number of training biopsy derived features 712*b* may be extracted from the training digitized biopsy data 704*a*. In some embodiments, the first number of training scan derived features 712*a* may be different than (e.g., greater than or less than) the second number of training biopsy derived features 712*b*. In other embodiments, the first number of training scan derived features 712*a* may be the same as the second number of training biopsy derived features 712*b*.

Training predictive features 714 are identified from the training derived features 712. The training predictive features 714 are features that have a relatively large impact on a prognosis for SCLC (e.g., a large prognostic impact on a response to chemotherapy). The training predictive features 714 comprise a set of features that are the same features for each of the plurality of preparatory patients. In some embodiments, the training predictive features 714 may comprise one or more training predictive scan derived features 714*a* identified from the training scan derived features 712*a* and one or more training predictive biopsy derived features 714*b* identified from the training biopsy derived features 712*b*.

A plurality of training RPRSs 716 are determined for each of the plurality of preparatory patients from training predictive features 714 associated with the patient. For example, a first RPRS may be calculated for a first patient based on training predictive features associated with the first patient, a second RPRS may be calculated for a second patient based on training predictive features associated with the second patient, etc. In some embodiments, the plurality of training RPRSs 716 may be calculated by way of a regression model (e.g., a Cox proportional hazard model) that is trained using the training predictive features 714 to form a risk score calculation model 715.

A risk score threshold 718 is determined from the plurality of training RPRSs 716. In some embodiments, the risk score threshold 718 may comprise a median risk score of the plurality of training RPRSs 716. Individual ones of the plurality of training RPRSs 716 may be compared to the risk score threshold 718 to stratify each preparatory patient of the first group of the plurality of preparatory patients within a plurality of different risk groups 428*a*. For example, individual patients having an RPRS that is below the risk score threshold 718 may be placed into a first risk group 430*a* that is indicative of a positive prognosis for SCLC (e.g., a positive response to chemotherapy for SCLC), while individual patients having an RPRS that is above the risk score threshold 718 may be placed into a second risk group 432*a* that is indicative of a negative prognosis for SCLC (e.g., a negative response to chemotherapy for SCLC).

The validation set 710 may be subsequently used to evaluate a performance of the plurality of different risk groups 428*a* determined by the training set 708. In such embodiments, validation derived features 720, including validation scan derived features 720*a* and validation biopsy derived features 720*b*, are extracted from validation scan data 702*b* and validation digitized biopsy data 704*b* of the second group of the plurality of preparatory patients within the validation set 710. Validation predictive features 722 are identified from the validation derived features 720. In some embodiments, the validation predictive features 722 may comprise one or more validation predictive scan derived features 722*a* and one or more validation predictive biopsy derived features 722*b*. In some embodiments, the validation predictive features are a same set of features as the training predictive features (shown by line 713).

A plurality of validation RPRSs 724 are determined for each patient of the second group of the plurality of preparatory patients. The plurality of validation RPRSs 724 may be determined by applying the risk score calculation model 715 determined by the training set 708 to the validation predictive features 722. The plurality of validation RPRSs 724 are compared to the risk score threshold 718 to determine placement of patients of the second group of the plurality of preparatory patients within a plurality of different risk groups 428*b* comprising a first risk group 430*b* and a second risk group 432*b*. The placement of the patients within the plurality of different risk groups 428*b* is subsequently analyzed to determine a prognostic ability of the different risk groups 428*b*.

In some embodiments, Kaplan-Meier survival analysis may be used to assess the prognostic ability of the different risk groups 428*b* on the validation set 710. In such embodiments, the Kaplan-Meier survival analysis is performed on each of the plurality of preparatory patients within the validation set and a result of the Kaplan-Meier survival analysis is compared to the risk groups to determine a prognostic ability of the different risk groups 428*b*. In some embodiments, clinical data may be used to assess the prognostic ability of the different risk groups 428*b* on the validation set 710.

Figure 8:
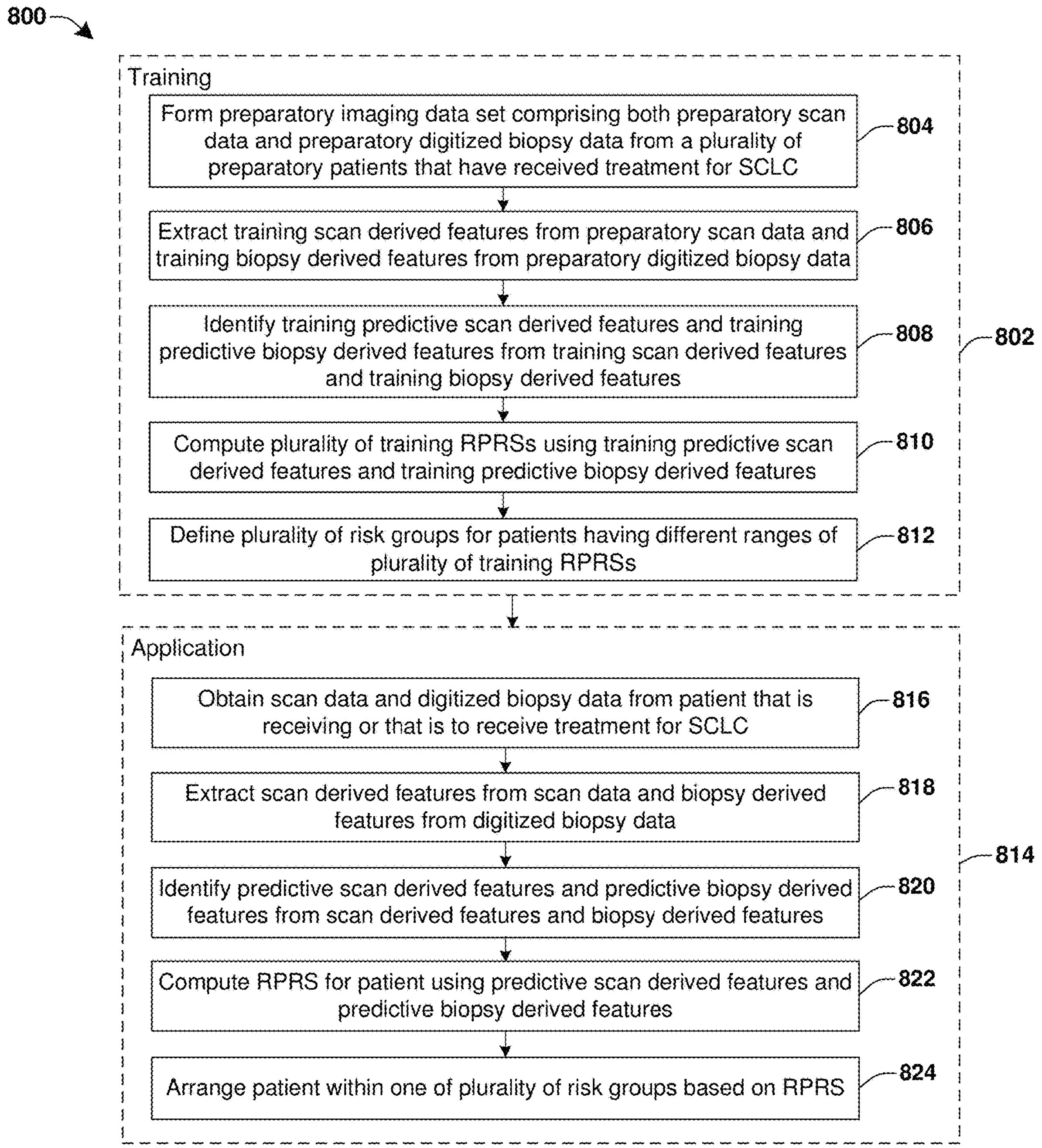
FIG. 8 illustrates some additional embodiments of a method of predicting a prognosis for a patient having SCLC utilizing features extracted from both scan data and digitized biopsy data.

FIG. 8 illustrates some additional embodiments of a method 800 of predicting a prognosis for a patient having SCLC utilizing features extracted from both scan data and digitized biopsy data.

While the disclosed methods (e.g., methods 100, 300, 600, and 800) are illustrated and described herein as a series of acts or events, it will be appreciated that the illustrated ordering of such acts or events are not to be interpreted in a limiting sense. For example, some acts may occur in different orders and/or concurrently with other acts or events apart from those illustrated and/or described herein. In addition, not all illustrated acts may be required to implement one or more aspects or embodiments of the description herein. Further, one or more of the acts depicted herein may be carried out in one or more separate acts and/or phases.

At 802, a training phase of the method 800 is performed to identify predictive features, to form a risk score calculation model, and to determine one or more risk score thresholds for different risk groups. In some embodiments, the training phase 802 may be performed according to acts 804-812.

At 804, a preparatory imaging data set is formed to comprise preparatory scan data and preparatory digitized biopsy data from a plurality of preparatory patients that have received treatment for SCLC.

At 806, training scan derived features are extracted from the preparatory scan data and training biopsy derived features are extracted from the preparatory digitized biopsy data.

At 808, training predictive scan derived features and training predictive biopsy derived features are identified from the training scan derived features and the training biopsy derived features, respectively.

At 810, a plurality of training RPRSs are determined from the training predictive scan derived features and the training predictive biopsy derived features. In some embodiments, the plurality of training RPRSs may be determined using a risk score calculation model formed by training a survival regression model with the training predictive scan derived features and the training predictive biopsy derived features.

At 812, a plurality of different risk groups are defined based on the plurality of training RPRSs. The different risk groups are defined to have different ranges of RPRSs. In some embodiments, the plurality of different risk groups may comprise a low risk group associated with a first range of RPRSs that is less than a median of the plurality of RPRSs and a high risk group associated with a second range of RPRSs that is greater than the median of the plurality of RPRSs.

At 814, an application phase 804 of the method is performed to apply the predictive features, the risk score calculation model, and the one or more risk score thresholds to a patient. In some embodiments, the application phase 804 may be performed according to acts 816-824.

At 816, scan data and digitized biopsy data is obtained for a patient that is receiving and/or that is to receive treatment for SCLC.

At 818, scan derived features are extracted from the scan data and biopsy derived features are extracted from digitized biopsy data.

At 820, predictive scan derived features and predictive biopsy derived features are identified from the scan derived features and the biopsy derived features. In some embodiments, the predictive scan derived features and predictive biopsy derived features are identified based on the training predictive scan derived features and training predictive biopsy derived features. In some embodiments, the predictive scan derived features and predictive biopsy derived features are the same features as the training predictive scan derived features and training predictive biopsy derived features.

At 822, an RPRS is computed for the patient using the predictive scan derived features and the predictive biopsy derived features. In some embodiments, the RPRS may be computed using the risk score calculation model developed in the training set (e.g., at 810).

At 824, the patient is arranged within one of plurality of risk groups based on the RPRS. The arrangement of the patient within a risk group provides a health care provider with guidance as to treatment of the patient.

Figure 9:
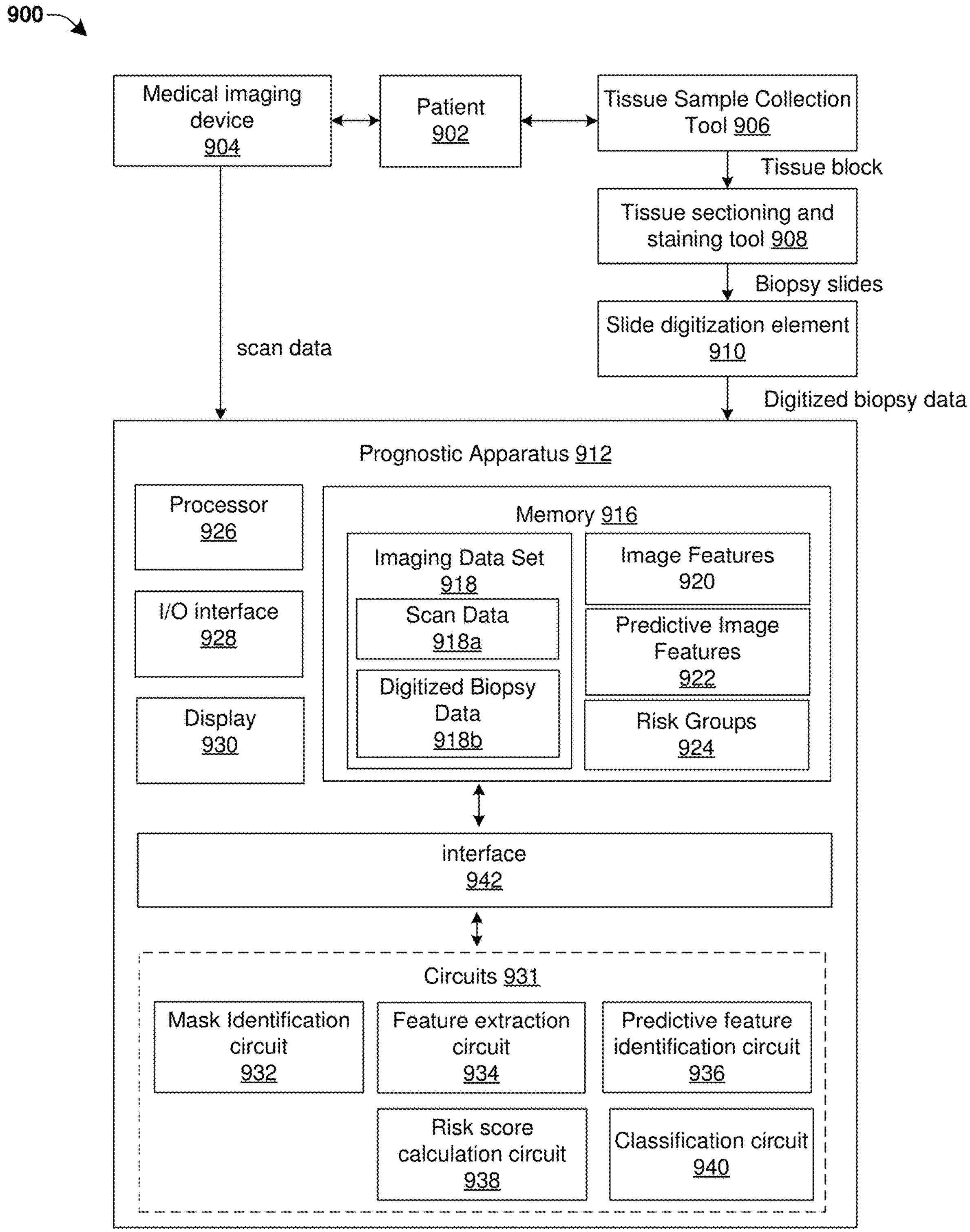
FIG. 9 illustrates some embodiments of an apparatus configured to predict a prognosis for a patient having SCLC utilizing features extracted from both scan data and digitized biopsy data.

FIG. 9 illustrates some additional embodiments of an apparatus 900 configured to predict a prognosis for a patient having SCLC utilizing features extracted from both scan data and digitized biopsy data.

The apparatus 900 comprises a prognostic apparatus 912. The prognostic apparatus 912 is coupled to a medical imaging device 904 that is configured to take radiological images of a patient 902. In various embodiments, the medical imaging device 904 may comprise an x-ray machine, a magnetic resonance imaging (MRI) scanner, a computerized tomography (CT) scanner, a positron emission tomography (PET) scanner, or the like.

The prognostic apparatus 912 is further coupled to slide digitization element 910 that is configured to obtain digitized images (e.g., whole slide images) of tissue samples collected from the patient 902. In some embodiments, one or more tissue samples (e.g., a tissue block) may be obtained using a tissue sample collection tool 906 (e.g., a cannular, forceps, needle, punch, or the like). The one or more tissue samples may be provided to a tissue sectioning and staining tool 908. In some embodiments, the tissue sectioning and staining tool 908 may be configured to slice the one or more tissue samples into thin slices that are placed on transparent slides (e.g., glass slides) to generate biopsy slides. The tissue on the biopsy slides is then stained by applying a dye. The dye may be applied on the posterior and anterior border of the sample tissues to locate the diseased or tumorous cells or other pathological cells. In some embodiments, the biopsy slides may comprise H&E (Hematoxylin and Eosin) stained slides. The slide digitization element 910 is configured to convert the biopsy slides to digitized biopsy data (e.g., whole slide images). In some embodiments, the slide digitization element 910 may comprise an image sensor (e.g., a photodiode, CMOS image sensor, or the like) that is configured to capture a digital image of the biopsy slides.

The prognostic apparatus 912 comprises a processor 926 and a memory 916. The processor 926 can, in various embodiments, comprise circuitry such as, but not limited to, one or more single-core or multi-core processors. The processor 926 can include any combination of general-purpose processors and dedicated processors (e.g., graphics processors, application processors, etc.). The processor(s) 926 can be coupled with and/or can comprise memory (e.g., memory 916) or storage and can be configured to execute instructions stored in the memory 916 or storage to enable various apparatus, applications, or operating systems to perform operations and/or methods discussed herein.

Memory 916 can be configured to store an imaging data set 918 comprising scan data 918*a* (e.g., CT, MRI, PET, SPECT, ultrasound, etc.) and digitized biopsy data 918*b* for a plurality of patients having SCLC. The scan data 918*a* and digitized biopsy data 918*b* can comprise images having a plurality of pixels, each pixel having an associated intensity. In some embodiments, the memory 916 can store a training set of images for training a classifier and/or a validation set of images.

The prognostic apparatus 912 also comprises an input/output (I/O) interface 928 (e.g., associated with one or more I/O devices), a display 930, a set of circuits 931, and an interface 942 that connects the processor 926, the memory 916, the I/O interface 928, and the set of circuits 931. I/O interface 928 can be configured to transfer data between the memory 916, the processor 926, the set of circuits 931, and external devices, for example, the medical imaging device 904. The display 930 is configured to output or display the prognosis the prognostic apparatus 912.

The set of circuits 931 can comprise a mask identification circuit 932, a feature extraction circuit 934, a predictive feature identification circuit 936, a risk score calculation circuit 938, and a classification circuit 940. The mask identification circuit 932 is configured to access the scan data 918*a* and/or the digitized biopsy data 918*b* and to identify lesional and/or perilesional masks within the scan data 918*a* and/or the digitized biopsy data 918*b*. Accessing the scan data 918*a* and/or the digitized biopsy data 918*b* can comprise accessing imaging data stored in the memory 916. In one embodiment, accessing the imaging data can include accessing imaging data stored in a data storage device, including a hard disk drive, a solid state device, a tape drive, or accessing radiological image(s) over a local area network, or accessing radiological image(s) over the internet. In some embodiments, the mask identification circuit 932 is configured to delineate (contour) metastases and use the delineated metastases to form images of lesional masks and perilesional masks. In some embodiments, the lesional masks and the perilesional masks may be stored in the memory 916.

In various embodiments, the feature extraction circuit 934 is configured to extract image features 920 from the scan data 918*a* and the digitized biopsy data 918*b*. The image features 920 may be stored in the memory 916. In some embodiments, the image features 920 may comprise scan derived features and biopsy derived features. In some embodiments, one or more of the image features 920 may be extracted from the lesional and/or perilesional masks within the scan data 918*a* and/or the digitized biopsy data 918*b*. In some embodiment, the feature extraction circuit 934 is configured to extract scan derived features and biopsy derived features using a gray level co-occurrence matrix (GLCM), as described above.

In various embodiments, the predictive feature identification circuit 936 is configured to determine predictive image features 922 from the image features 920. The predictive image features 922 may be stored in the memory 916. In some embodiments, the predictive image features 922 may comprise predictive scan derived features and predictive biopsy derived features. The predictive scan derived features and predictive biopsy derived features are a subset of the scan derived features and biopsy derived features that are most predictive of a response to chemotherapy for SCLC. In some embodiments, the predictive feature identification circuit 936 is configured to determine predictive scan derived features and predictive biopsy derived features using a random forest algorithm.

In various embodiments, the risk score calculation circuit 938 is configured to determine a RPRS from the predictive image features 922 (e.g., both the predictive scan derived features and predictive biopsy derived features). In some embodiments, the risk score calculation circuit 938 may use an elastic net regularized Cox proportional hazards model to derive the RPRS.

A classification circuit 940 is configured to classify patients into risk groups 924 based on their RPRS. The classification circuit 940 may be configured to classify patients into a first group having a favorable prognosis (e.g., that responds favorably to chemoradiation therapy for SCLC), and a second group having an unfavorable prognosis (e.g., that responds poorly to chemoradiation therapy for SCLC). In some embodiments, the classification circuit 940 may classify the patients by comparing RPRS of a patient to a risk score threshold. In some embodiments, the risk score threshold may be derived within the training set to stratify the RPRS within a plurality of different risk groups (e.g., within a low risk group and a high risk group).

Example Use Case 1:

The following discussion provides example embodiments in connection with a first example use case involving a method of utilizing features from both imaging and digitized biopsy to determine a prognosis of patients that are receiving or that are to receive chemoradiation therapy for SCLC.

Methods

Seventy-eight patients with extensive and limited-stage SCLC who received platinum-doublet chemotherapy were selected. Objective response to chemotherapy (RECIST criteria) and overall survival (OS) as clinical endpoints were available for 51 and 78 patients respectively. The patients were divided randomly into two sets (Training (Sd), Validation (Sv)) with a constraint (equal number of responders and nonresponders in Sd)—Sd comprised twenty-one patients with SCLC. Sv included thirty patients. CT scans and digitized Hematoxylin Eosin-stained (H&E) biopsy images were acquired for each patient. A set of CT derived (46%) and tissue derived (53%) image features were captured. These included shape and textural patterns of the tumoral and peritumoral regions from CT scans and of tumor regions on H&E images. A random forest feature selection and linear regression model were used to identify the most predictive CT and H&E derived image features associated with chemotherapy response from Sd. A Cox proportional hazard regression model was used with these features to compute a RPRS for each patient in Sd. Patients in Sv were stratified into high and low-risk groups based on a risk score threshold (e.g., a median risk score). Kaplan-Meier survival analysis was used to assess the prognostic ability of the RPRS on Sv.

Result

The RPRS was determined from nine CT (intra and peri-tumoral texture) and six H&E derived (cancer cell texture and shape) features. A linear regression model in conjunction with these 15 features was significantly associated with chemo-sensitivity in Sv (AUC=0.76, PRC=0.81). A multivariable model with these 15 features was significantly associated with OS in Sv (HR=2.5, 95% CI: 1.3-4.9, P=0.0043). Kaplan-Meier survival analysis revealed a significantly reduced OS in the high-risk group compared to the low-risk group.

Therefore, the present disclosure relates to a method of predicting a prognosis for a patient having small cell lung cancer (SCLC) utilizing a radiomic-pathomic risk score (RPRS) determined from both radiomic features extracted from scan data and pathomic features extracted from digitized biopsy data.

In some embodiments, the disclosure relates to a non-transitory computer-readable medium storing computer-executable instructions that, when executed, cause a processor to perform operations, including generating an imaging data set having both scan data and digitized biopsy data from a patient having small cell lung cancer (SCLC); extracting scan derived features from the scan data; extracting biopsy derived features from the digitized biopsy data; and calculating a radiomic-pathomic risk score (RPRS) from one or more of the scan derived features and one or more of the biopsy derived features, the RPRS being indicative of a prognosis of the patient. In some embodiments, the non-transitory computer-readable medium further includes utilizing a machine learning classifier to identify predictive scan derived features from the scan derived features and predictive biopsy derived features from the biopsy derived features; and calculating the RPRS from both the predictive scan derived features and the predictive biopsy derived features. In some embodiments, the non-transitory computer-readable medium further includes identifying a first lesional mask and a first perilesional mask of the scan data; and extracting the scan derived features from the first lesional mask and the first perilesional mask. In some embodiments, the digitized biopsy data includes digitized Hematoxylin and Eosin (H&E) images. In some embodiments, the non-transitory computer-readable medium further includes arranging the patient into one of a plurality of different risk groups based upon the RPRS. In some embodiments, the non-transitory computer-readable medium further includes generating a preparatory imaging data set to have preparatory scan data and preparatory digitized biopsy data from a plurality of preparatory patients having SCLC; extracting training scan derived features from the preparatory scan data; extracting training biopsy derived features from the preparatory digitized biopsy data; and calculating a plurality of training radiomic-pathomic risk scores for the plurality of preparatory patients from the training scan derived features and the training biopsy derived features. In some embodiments, the non-transitory computer-readable medium further includes determining a median risk score of the plurality of training radiomic-pathomic risk scores; and arranging the patient into one of a plurality of different risk groups by comparing the RPRS to the median risk score. In some embodiments, the non-transitory computer-readable medium further includes determining a predicted response to chemotherapy treatment for the patient using the RPRS.

In other embodiments, the disclosure relates to a method of predicting a prognosis of small cell lung cancer (SCLC), including taking a radiological image of a region of interest of a patient having SCLC, the radiologic image including scan data; taking a tissue sample from the region of interest of the patient; digitizing the tissue sample to form digitized biopsy data; extracting scan derived features from the scan data;

extracting biopsy derived features from the digitized biopsy data; identifying predictive scan derived features from the scan derived features and predictive biopsy derived features from the biopsy derived features; and calculating an RPRS from both the predictive scan derived features and the predictive biopsy derived features, the RPRS being indicative of a prognosis of the patient. In some embodiments, the patient has not received chemotherapy for the SCLC prior to taking the radiological image and the tissue sample. In some embodiments, the method further includes identifying a first lesional mask and a first perilesional mask of the scan data; and extracting the scan derived features from both the first lesional mask and the first perilesional mask. In some embodiments, the predictive scan derived features or the predictive biopsy derived features may include Haralick features. In some embodiments, the scan derived features consist of texture features; and the biopsy derived features consist of shape features. In some embodiments, the scan derived features include texture features and shape features; and the biopsy derived features include texture features and shape features. In some embodiments, one or more of the scan derived features are extracted using a gray level co-occurrence matrix (GLCM).

In yet other embodiments, the disclosure relates to a prognostic apparatus configured to predict a prognosis for a patient having small cell lung cancer (SCLC), including a memory configured to store an imaging data set having both scan data and digitized biopsy data from a patient having SCLC; a feature extraction circuit configured to extract scan derived features from the scan data and biopsy derived features from the digitized biopsy data; a risk score calculation circuit configured to calculate an RPRS from one or more of the scan derived features and from one or more of the biopsy derived features; and a classification circuit configured to arrange the patient into one of a plurality of different risk groups based upon the RPRS. In some embodiments, the prognostic apparatus further includes a predictive feature identification circuit configured to identify predictive scan derived features from the scan derived features and predictive biopsy derived features from the biopsy derived features; and the risk score calculation circuit being configured to calculate the RPRS from both the predictive scan derived features and the predictive biopsy derived features. In some embodiments, the prognostic apparatus further includes a mask identification circuit configured to identify a first lesional mask and a first perilesional mask of the scan data; and the feature extraction circuit being configured to extract the scan derived features from the first lesional mask and the first perilesional mask. In some embodiments, the digitized biopsy data includes digitized Hematoxylin and Eosin (H&E) images. In some embodiments, the risk score calculation circuit is further configured to determine a median risk score of a plurality of training radiomic-pathomic risk scores determined from imaging data of a plurality of preparatory patients; and the classification circuit is configured to arrange the patient into one of the plurality of different risk groups by comparing the RPRS to the median risk score.

Examples herein can include subject matter such as an apparatus, a digital whole slide scanner, a CT system, an MRI system, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for predicting SCLC treatment response, according to embodiments and examples described.

References to "one embodiment", "an embodiment", "one example", and "an example" indicate that the embodiment (s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action (s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable medium storing computer-executable instructions that, when executed, cause a processor to perform operations, comprising:

generating an imaging data set comprising both scan data and digitized biopsy data from a patient having small cell lung cancer (SCLC), wherein the scan data includes data from a radiological scan of the patient;

extracting scan derived features from the scan data;

extracting biopsy derived features from the digitized biopsy data; and calculating a radiomic-pathomic risk score (RPRS) from one or more of the scan derived features and one or more of the biopsy derived features, wherein the RPRS is indicative of a prognosis of the patient.

2. The non-transitory computer-readable medium of claim 1, further comprising:

utilizing a machine learning classifier to identify predictive scan derived features from the scan derived features and predictive biopsy derived features from the biopsy derived features; and calculating the RPRS from both the predictive scan derived features and the predictive biopsy derived features.

3. The non-transitory computer-readable medium of claim 1, further comprising:

identifying a first lesional mask and a first perilesional mask of the scan data; and extracting the scan derived features from the first lesional mask and the first perilesional mask.

4. The non-transitory computer-readable medium of claim 1, wherein the digitized biopsy data comprises digitized Hematoxylin and Eosin (H&E) images.

5. The non-transitory computer-readable medium of claim 1, wherein the radiological scan comprises an x-ray, a computerized tomography (CT) scan, a magnetic resonance imaging (MRI) scan, or a positron emission tomography (PET) scan.

6. The non-transitory computer-readable medium of claim 1, further comprising:

generating a preparatory imaging data set to comprise preparatory scan data and preparatory digitized biopsy data from a plurality of preparatory patients having SCLC;

extracting training scan derived features from the preparatory scan data;

extracting training biopsy derived features from the preparatory digitized biopsy data; and calculating a plurality of training radiomic-pathomic risk scores for the plurality of preparatory patients from the training scan derived features and the training biopsy derived features.

7. The non-transitory computer-readable medium of claim 6, further comprising:

determining a median risk score of the plurality of training radiomic-pathomic risk scores; and arranging the patient into one of a plurality of different risk groups by comparing the RPRS to the median risk score.

8. The non-transitory computer-readable medium of claim 1, further comprising:

determining a predicted response to chemotherapy treatment for the patient using the RPRS.

9. A method of predicting a prognosis of small cell lung cancer (SCLC), comprising:

taking a radiological image of a region of interest of a patient having SCLC, the radiologic image comprising scan data;

taking a tissue sample from the region of interest of the patient;

digitizing the tissue sample to form digitized biopsy data;

extracting scan derived features from the scan data;

extracting biopsy derived features from the digitized biopsy data;

identifying predictive scan derived features from the scan derived features and predictive biopsy derived features from the biopsy derived features; and calculating an RPRS from both the predictive scan derived features and the predictive biopsy derived features, wherein the RPRS is indicative of a prognosis of the patient.

10. The method of claim 9, wherein the patient has not received chemotherapy for the SCLC prior to taking the radiological image and the tissue sample.

11. The method of claim 9, further comprising:

identifying a first lesional mask and a first perilesional mask of the scan data; and extracting the scan derived features from both the first lesional mask and the first perilesional mask.

12. The method of claim 9, wherein the predictive scan derived features or the predictive biopsy derived features may comprise Haralick features.

13. The method of claim 9, wherein the scan derived features consist of texture features; and wherein the biopsy derived features consist of shape features.

14. The method of claim 9, wherein the scan derived features comprise texture features and shape features; and wherein the biopsy derived features comprise texture features and shape features.

15. The method of claim 9, wherein the radiological image comprises an x-ray, a computerized tomography (CT) scan, a magnetic resonance imaging (MRI) scan, or a positron emission tomography (PET) scan.

16. A prognostic apparatus configured to predict a prognosis for a patient having small cell lung cancer (SCLC), comprising:

a memory configured to store an imaging data set comprising both scan data and digitized biopsy data from a patient having SCLC, wherein the scan data includes data from a radiological scan of the patient;

a feature extraction circuit configured to extract scan derived features from the scan data and biopsy derived features from the digitized biopsy data;

a risk score calculation circuit configured to calculate an RPRS from one or more of the scan derived features and from one or more of the biopsy derived features; and a classification circuit configured to arrange the patient into one of a plurality of different risk groups based upon the RPRS.

17. The prognostic apparatus of claim 16, further comprising:

a predictive feature identification circuit configured to identify predictive scan derived features from the scan derived features and predictive biopsy derived features from the biopsy derived features; and wherein the risk score calculation circuit is configured to calculate the RPRS from both the predictive scan derived features and the predictive biopsy derived features.

18. The prognostic apparatus of claim 16, further comprising:

a mask identification circuit configured to identify a first lesional mask and a first perilesional mask of the scan data; and wherein the feature extraction circuit is configured to extract the scan derived features from the first lesional mask and the first perilesional mask.

19. The prognostic apparatus of claim 16, wherein the digitized biopsy data comprises digitized Hematoxylin and Eosin (H&E) images.

20. The prognostic apparatus of claim 16, wherein the risk score calculation circuit is further configured to determine a median risk score of a plurality of training radiomic-pathomic risk scores determined from imaging data of a plurality of preparatory patients; and wherein the classification circuit is configured to arrange the patient into one of the plurality of different risk groups by comparing the RPRS to the median risk score.

* * * * *

UNITED STATES PATENT AND TRADEMARK OFFICE

CERTIFICATE OF CORRECTION

PATENT NO. : 12,159,403 B2
APPLICATION NO. : 17/670817
DATED : December 3, 2024
INVENTOR(S) : Anant Madabhushi et al.

It is certified that error appears in the above-identified patent and that said Letters Patent is hereby corrected as shown below:

On the Title Page

Column 1, under Assignee, please add Case Western Reserve University, Cleveland, OH (US); and University Hospitals Cleveland Medical Center, Cleveland, OH (US).

Signed and Sealed this
Fourth Day of March, 2025

Coke Morgan Stewart
*Acting Director of the United States Patent and Trademark Office*